(12) United States Patent
Kennedy et al.

(10) Patent No.: US 7,910,129 B2
(45) Date of Patent: Mar. 22, 2011

(54) CARBODIIMIDE CROSSLINKING OF FUNCTIONALIZED POLYETHYLENE GLYCOLS

(75) Inventors: John Kennedy, Guilford, CT (US); Mark S. Roby, Killingsworth, CT (US); Ahmad R. Hadba, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/635,344

(22) Filed: Dec. 6, 2006

(65) Prior Publication Data

US 2007/0148128 A1  Jun. 28, 2007

Related U.S. Application Data

(60) Provisional application No. 60/742,935, filed on Dec. 6, 2005.

(51) Int. Cl.
*A61F 13/00* (2006.01)

(52) U.S. Cl. ........................................................ 424/443

(58) Field of Classification Search .................. None
See application file for complete search history.

(56) References Cited

U.S. PATENT DOCUMENTS

| | | | |
|---|---|---|---|
| 3,773,595 A | 11/1973 | Burba et al. |
| 3,879,493 A | 4/1975 | Mudde |
| 3,903,232 A | 9/1975 | Wood et al. |
| 3,976,055 A | 8/1976 | Cartmell et al. |
| 4,057,535 A | 11/1977 | Lipatova et al. |
| 4,061,662 A | 12/1977 | Marans et al. |
| 4,132,839 A | 1/1979 | Marans et al. |
| 4,169,175 A | 9/1979 | Marans et al. |
| 4,321,350 A | 3/1982 | Lehmann |
| 4,323,491 A | 4/1982 | Veselovsky et al. |
| 4,404,296 A | 9/1983 | Schapel |
| 4,451,627 A | 5/1984 | Frisch, Jr. et al. |
| 4,477,604 A | 10/1984 | Oechsle, III |
| 4,511,626 A | 4/1985 | Schumacher |
| 4,547,561 A | 10/1985 | Wegner |
| 4,654,409 A | 3/1987 | Shirai et al. |
| 4,681,934 A | 7/1987 | Shibanai et al. |
| 4,722,815 A | 2/1988 | Shibanai |
| 4,740,534 A | 4/1988 | Matsuda et al. |
| 4,762,899 A | 8/1988 | Shikinami |
| 4,804,691 A | 2/1989 | English et al. |
| 4,806,614 A | 2/1989 | Matsuda et al. |
| 4,829,099 A | 5/1989 | Fuller et al. |
| 4,883,837 A | 11/1989 | Zabrocki |
| 4,994,208 A | 2/1991 | McBain et al. |
| 4,994,542 A | 2/1991 | Matsuda et al. |
| 4,997,656 A | 3/1991 | Shikinami et al. |
| 5,065,752 A | 11/1991 | Sessions et al. |
| 5,082,663 A | 1/1992 | Konishi et al. |
| 5,166,300 A | 11/1992 | Rumon et al. |
| 5,169,720 A | 12/1992 | Braatz et al. |
| 5,173,301 A | 12/1992 | Itoh et al. |
| 5,175,228 A | 12/1992 | Wang et al. |
| 5,204,110 A | 4/1993 | Cartmell et al. |
| 5,346,981 A | 9/1994 | Sarpeshkar et al. |
| 5,374,704 A | 12/1994 | Muller et al. |
| 5,389,718 A | 2/1995 | Potter et al. |
| 5,416,193 A * | 5/1995 | Desai ........................... 530/334 |
| 5,457,141 A | 10/1995 | Matsuda |
| 5,462,536 A | 10/1995 | Braatz et al. |
| 5,574,104 A | 11/1996 | Kolycheck et al. |
| 5,574,123 A | 11/1996 | Bock et al. |
| 5,578,662 A | 11/1996 | Bennett et al. |
| 5,603,798 A | 2/1997 | Bhat |
| 5,665,477 A | 9/1997 | Meathrel et al. |
| 5,672,652 A | 9/1997 | Bhat |
| 5,688,860 A | 11/1997 | Croft |
| 5,717,030 A | 2/1998 | Dunn et al. |
| 5,780,573 A | 7/1998 | Iwata et al. |
| 5,791,352 A | 8/1998 | Reich et al. |
| 5,795,633 A | 8/1998 | Yokoyama et al. |
| 5,846,214 A | 12/1998 | Makuuchi et al. |
| 5,869,566 A | 2/1999 | Thomas |
| 5,900,245 A | 5/1999 | Sawhney et al. |
| 5,900,473 A | 5/1999 | Acevedo et al. |
| 5,912,193 A | 6/1999 | Iwata et al. |
| 5,922,809 A | 7/1999 | Bhat et al. |
| 5,948,427 A | 9/1999 | Yamamoto et al. |
| 5,976,305 A | 11/1999 | Bhat et al. |
| 5,990,237 A | 11/1999 | Bentley et al. |
| 6,071,530 A | 6/2000 | Polson |
| 6,071,538 A * | 6/2000 | Milstein et al. ............... 424/464 |
| 6,103,850 A | 8/2000 | Reichel et al. |
| 6,149,931 A | 11/2000 | Schwartz et al. |

(Continued)

FOREIGN PATENT DOCUMENTS

EP    0 077 192 A2    4/1983

(Continued)

OTHER PUBLICATIONS

Margolin A L et al.: "Steroselective Oligomerizations Catalyzed by Lipases In Organic Olvents"; Tetrahedron Letters, vol. 28, No. 15, 1987pp. 1607-1610.
Okumura S. et al.: "Synthesis of Ester Oligomer by *Aspergillniger* Lipase" Agricultural and Biological Chemistry, vol. 48, No. 11, 1984, pp. 2805-2808.
Lumann N R et al.: The convergent Synthesis of Poly(glycerol-succininc acid) Dendritic Marcomolecules: Chemistry—A European Journal, VCH Publishers, US vol. 9, 2003, pp. 5618-5626.
Database WPI, Section Ch, Week 199442 Derwent Publications Ltd. London, GB; AN 1994-3383493.
Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.
Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.

(Continued)

*Primary Examiner* — Michael G Hartley
*Assistant Examiner* — Paul Dickinson

(57) ABSTRACT

A synthetic composition is provided which includes an acid-functional polymer having at least one pendant acid group, an amine-functional polymer having at least one pendant amine group, and a coupling agent. The synthetic composition can be used in human and animal medical applications as an adhesive or sealant.

24 Claims, No Drawings

U.S. PATENT DOCUMENTS

| | | | |
|---|---|---|---|
| 6,154,089 A | 11/2000 | Rombach | |
| 6,162,241 A | 12/2000 | Coury et al. | |
| 6,197,915 B1 | 3/2001 | Yamana et al. | |
| 6,217,894 B1 | 4/2001 | Sawhney et al. | |
| 6,235,815 B1 | 5/2001 | Loercks et al. | |
| 6,261,544 B1 | 7/2001 | Coury et al. | |
| 6,290,729 B1 | 9/2001 | Sleplan et al. | |
| 6,296,908 B1 | 10/2001 | Reihs et al. | |
| 6,297,349 B1 | 10/2001 | Goldberg et al. | |
| 6,312,725 B1 | 11/2001 | Wallace et al. | |
| 6,352,710 B2 | 3/2002 | Sawhney et al. | |
| 6,395,112 B1 | 5/2002 | Sitzmann et al. | |
| 6,433,054 B1 | 8/2002 | Kawaguchi et al. | |
| 6,461,631 B1 | 10/2002 | Dunn et al. | |
| 6,465,001 B1 | 10/2002 | Hubbell et al. | |
| 6,465,004 B1 | 10/2002 | Rossi-Montero et al. | |
| 6,495,127 B1 | 12/2002 | Wallace et al. | |
| 6,512,033 B1 | 1/2003 | Wu | |
| 6,555,645 B1 | 4/2003 | Ikeda et al. | |
| 6,565,969 B1 | 5/2003 | Lamon et al. | |
| 6,576,702 B2 | 6/2003 | Anderle et al. | |
| 6,579,952 B1 | 6/2003 | Niki et al. | |
| 6,582,713 B2 | 6/2003 | Newell et al. | |
| 6,605,666 B1 | 8/2003 | Scholz et al. | |
| 6,824,703 B2 | 11/2004 | Lawrey et al. | |
| 2002/0022883 A1 | 2/2002 | Burg | |
| 2002/0028875 A1 | 3/2002 | Anderle et al. | |
| 2002/0071855 A1 | 6/2002 | Sadozai et al. | |
| 2002/0127196 A1 | 9/2002 | Avila et al. | |
| 2003/0032734 A1 | 2/2003 | Roby | |
| 2003/0035786 A1 | 2/2003 | Hendriks et al. | |
| 2003/0044380 A1 | 3/2003 | Zhu et al. | |
| 2003/0176615 A1 | 9/2003 | Lawrey et al. | |
| 2003/0195293 A1 | 10/2003 | Lubnin et al. | |
| 2004/0019178 A1 | 1/2004 | Gross et al. | |
| 2004/0023842 A1 | 2/2004 | Pathak et al. | |
| 2004/0068078 A1 | 4/2004 | Milbocker | |
| 2004/0092695 A1 | 5/2004 | Hu et al. | |
| 2004/0198901 A1 | 10/2004 | Graham et al. | |
| 2004/0198944 A1 | 10/2004 | Meltzer et al. | |
| 2004/0242831 A1 | 12/2004 | Tian et al. | |
| 2004/0259968 A1 | 12/2004 | Krebs | |
| 2005/0004661 A1 | 1/2005 | Lewis et al. | |
| 2005/0069573 A1 | 3/2005 | Cohn et al. | |
| 2005/0070913 A1 | 3/2005 | Milbocker et al. | |
| 2005/0129733 A1 | 6/2005 | Milbocker et al. | |
| 2005/0131192 A1 | 6/2005 | Matsuda et al. | |
| 2005/0142162 A1 | 6/2005 | Hunter et al. | |
| 2005/0147647 A1 | 7/2005 | Glauser et al. | |
| 2005/0154148 A1 | 7/2005 | Nakamichi et al. | |
| 2005/0266086 A1 | 12/2005 | Sawhney | |
| 2006/0013797 A1* | 1/2006 | Shen | 424/78.08 |

FOREIGN PATENT DOCUMENTS

| | | | |
|---|---|---|---|
| EP | 0 482 467 A2 | | 4/1992 |
| EP | 0 488 629 A1 | | 6/1992 |
| EP | 0 301 516 B1 | | 9/1992 |
| EP | 0 625 034 B1 | | 5/2002 |
| EP | 1 391 205 A1 | | 2/2005 |
| EP | 1 719 530 A | | 11/2006 |
| EP | 1857489 A1 | | 11/2007 |
| GB | 985 144 | | 3/1965 |
| JP | 6263850 | | 9/1994 |
| JP | 2002060341 | | 2/2002 |
| WO | WO 0033764 A1 | * | 6/2000 |
| WO | WO 00/43050 A1 | | 7/2000 |
| WO | WO 01/00246 A | | 1/2001 |
| WO | WO 01/16210 A | | 3/2001 |
| WO | WO 02/056790 A2 | | 7/2002 |
| WO | WO 03/011173 A2 | | 2/2003 |
| WO | WO 03/011173 A3 | | 2/2003 |
| WO | WO 2004/039323 A2 | | 5/2004 |
| WO | WO 2004/039323 A3 | | 5/2004 |
| WO | WO 2004/039857 A1 | | 5/2004 |
| WO | WO 2004/041890 A1 | | 5/2004 |
| WO | WO 2005/032461 A2 | | 4/2005 |
| WO | WO 2005/100429 A1 | | 10/2005 |
| WO | WO 2006/010278 A1 | | 2/2006 |
| WO | WO 2006/084911 A2 | | 8/2006 |
| WO | WO 2006/107957 A2 | | 10/2006 |
| WO | WO 2006/128742 A2 | | 12/2006 |
| WO | WO 2006/128918 A1 | | 12/2006 |
| WO | WO 2007/001448 A2 | | 1/2007 |
| WO | WO 2007/067623 A | | 6/2007 |
| WO | WO 2008/047100 A1 | | 4/2008 |

OTHER PUBLICATIONS

M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.

Mei Xuan Xu et al.: Synthesis and Properties of Unsaturated Polyester Dio-Polyurethanehybrid Polymer Network: Journal of Applied Polymer Science, John Wiley and Sons Inc. New York, US, vol. 54, No. 11, Dec. 12, 1994, pp. 1659-1663.

Oprea S. et al.: "Poly(urethane-methacrylates)s. Synthesis and Characterization"; Polymer, Elsevier Science Publishers B.V., GB, vol. 42, No. 17, Aug. 2001, pp. 7257-7266.

European Search Report for Appln. No. EP 08 25 3647 completed Mar. 6, 2009.

European Search Report for Appln. No. EP 08 25 1790.5 completed Jun. 19, 2009.

International Search Report from European Application No. EP 06 84 4894 date of completion Jun. 9, 2010.

International Search Report from European Application No. EP 06 84 4890 date of completion Jun. 4, 2010.

* cited by examiner

CARBODIIMIDE CROSSLINKING OF FUNCTIONALIZED POLYETHYLENE GLYCOLS

CROSS-REFERENCE TO RELATED APPLICATIONS

This application claims the benefit of U.S. Provisional Patent Application No. 60/742,935 filed Dec. 6, 2005, the entire disclosure of which is incorporated by reference herein.

BACKGROUND

1. Technical Field

The present disclosure relates to crosslinked compositions made from synthetic polymers and the use of such compositions as biological adhesives and/or sealants.

2. Background of Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that, in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as a tissue adhesive or tissue sealant are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive that is fully synthetic and therefore highly consistent in its properties without the concern of viral transmission. Such an adhesive should be flexible and biocompatible and should be suitable for use as an adhesive or sealant.

SUMMARY

New and useful synthetic macromer compositions for use in connection with living tissue as adhesives or sealants are described herein. The synthetic macromer composition contains a first polymer having at least one pendant acid group, a second polymer having at least one pendant amine group, and a coupling agent. The coupling agent may be a carbodiimide, in embodiments EDC (1-ethyl-3(3-dimethyl-amino propyl)-carbodiimide hydrochloride).

In embodiments, the macromer composition of the present disclosure may include an acid-functional polymer of formula

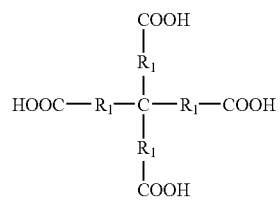

where $R_1$ can be the same or different at each location and can be hydrogen, polyalkylene oxides, polyethylene glycols having degradable linkages, and polyethylene oxide-polypropylene oxide copolymers, in combination with an amine-functional polymer which can include polyalkylene oxides having at least one pendant amine group and polyamino acids having at least one pendant amine group, and a coupling agent.

In embodiments, the amine-functional polymer utilized in a composition of the present disclosure may include a compound of formula:

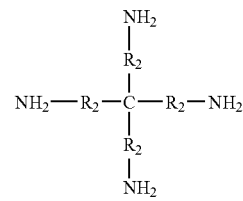

where $R_2$ can be the same or different at each location and can be hydrogen, polyalkylene oxides, polyethylene glycols having degradable linkages, and polyethylene oxide-polypropylene oxide copolymers.

Methods for adhering and/or forming a seal between two tissue surfaces in an animal are also described. The methods include the steps of approximating a first tissue surface with a second tissue surface and applying the synthetic absorbable macromer composition in contact with both the first and second tissue surfaces. The synthetic absorbable macromer composition applied to the tissue contains a polymer that includes pendant acid groups, a second polymer that includes pendant amine groups and a coupling agent.

In other embodiments, the present synthetic absorbable macromer compositions may be used to secure a medical device to tissue. The medical device, for example an implant, may be approximated with a first animal tissue surface and the disclosed synthetic absorbable macromer composition may be applied in contact with both the device and the tissue surface.

The present synthetic absorbable macromer compositions can also be used as sealants or void fillers to fill a defect within animal tissue. The synthetic absorbable macromer composition can also be used as a sealant for air and/or fluid leaks, and can be particularly useful for use with delicate tissues where sutures, clamps or other conventional tissue closure mechanisms may cause further tissue damage.

DETAILED DESCRIPTION

The fully synthetic absorbable macromer compositions described herein may be useful for adhering animal tissue or sealing voids in animal tissue and include at least three components; namely, a first polymer having at least one pendant acid group, a second polymer having at least one pendant amine group, and at least one coupling agent. The resulting adhesive or sealant can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

The first polymer utilized in the synthetic absorbable macromer compositions herein possesses at least one pendant acid group and thus may be referred to, in embodiments, as an acid-functional polymer. The pendant acid groups can be primary or secondary carboxyl groups, or mixtures thereof. Suitable polymers include polyalkylene oxides with pendant carboxylic acid groups, and polyamino acids including, but not limited to, polyglutamic acid, polyaspartic acid, and synthetic amino acids with pendant acidic groups, including those commercially available from Sigma-Aldrich (St. Louis, Mo.). Other suitable polymers which may be utilized include, but are not limited to, poly(acrylic acid), poly(methacrylic acid), poly(maleic acid), and poly(itaconic acid). Also useful are block or random copolymers of at least one vinyl monomer with an acid such as (meth)acrylic acid, acrylic acid, maleic acid or itaconic acid.

Where a polyalkylene oxide is utilized, the polyalkylene oxide backbone can be derived from any $C_2$-$C_6$ alkylene oxide and can be homopolymeric or copolymeric. Thus, for example, the polyalkylene oxide backbone can be derived from ethylene oxide and be a polyethylene oxide (PEO) backbone. As another example, the polyalkylene oxide backbone can be derived from propylene oxide and be a polypropylene oxide (PPO) backbone. As yet another example, a combination of ethylene oxide and propylene oxide can be used to form a random or block copolymer as the backbone. The molecular weight of the polyalkylene oxide backbone should be chosen to provide desired physical characteristics to the final compound. Suitable backbones have molecular weights in the range of from about 500 to about 20,000, in embodiments from about 1000 to about 10,000, typically from about 2000 to about 5000.

In one embodiment the acid-functional polymer can correspond to the following formula (I):

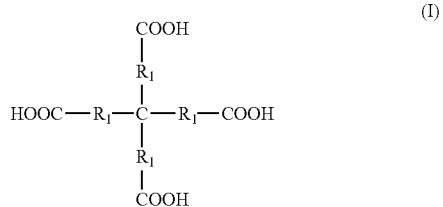

(I)

where $R_1$ can be the same or different at each location and may be hydrogen, a polyalkylene oxide, polyethylene glycols having degradable linkages, or a poloxamer such as polyethylene oxide (PEO) copolymer with polypropylene oxide (PPO), including the triblock PEO—PPO copolymers commercially available as PLURONICS® from BASF Corporation (Mt. Olive, N.J.).

Methods for producing these acid-functional polymers are known to those skilled in the art. Such polymers are also commercially available from Sigma-Aldrich (St. Louis, Mo.).

In one embodiment, the polyalkylene oxide may be a polyethylene oxide such as a polyethylene glycol ("PEG"). As used herein, polyethylene glycol generally refers to a polymer with a molecular weight of less than 50,000, while polyethylene oxide is used for higher molecular weights. PEGs provide excellent water retention, flexibility and viscosity in the synthetic absorbable macromer composition. Suitable PEGs include di-functional materials, tri-functional materials, tetra-functional materials, and combinations thereof. In embodiments, the PEG is a mixture of di-, tri- and tetra-functional materials.

In embodiments, the PEG may be terminated with at least one carboxylic acid end group such as formic acid, acetic acid, propionic acid, butyric acid, stearic acid, benzoic acid, toluic acid, salicylic acid, and combinations thereof.

In some embodiments, the PEG may have degradable linkages. Suitable degradable linkages include, but are not limited to, hydrolytically labile α-hydroxy acids such as lactic acid, glycolic acid, and hydroxy-butyric acid, glycolide, lactide, lactones including ε-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides including sebacic acid anhydride and azelaic acid anhydride, etc. and combinations thereof. Those skilled in the art will readily envision reaction schemes for incorporating these components into the acid-functional polymer, the second polymer, or both.

The acid-functional polymer should have a molecular weight sufficiently high that, when crosslinked, the synthetic absorbable macromer composition provides adequate adhesive properties, but sufficiently low that upon degradation the resulting polymer fragments can be excreted by the body. The molecular weight of the acid-functional polymer can range from about 500 to about 20,000, typically from about 1,000 to about 5,000.

The acid-functional polymer component may be present in the adhesive composition of the present disclosure in amounts ranging from about 80% to about 20% by weight of the adhesive composition, in embodiments from about 75% to about 33% by weight of the adhesive composition, typically from about 66% to about 50% by weight of the adhesive composition.

The second component of the synthetic absorbable macromer composition of the present disclosure is a polymer possessing reactive amine groups and thus may be referred to, in embodiments, as an amine-functional polymer. The pendant amine groups can be primary or secondary amine groups, or combinations thereof. Suitable amine-functional polymers include polyalkylene oxides having pendant amine groups, and polyamino acids having basic amine side chains such as polylysine, polyornithine, polycysteine, polyarginine, polyhistidine, polyallyl amines, and synthetic polypeptides having pendant amine groups, including those commercially available from Sigma-Aldrich (St. Louis, Mo.), and combinations thereof. Also useful are block or random copolymers of at least one monomer having no amine substitution with an amine such as lysine, ornithine or allylamine.

In one embodiment, where the amine-functional polymer is a polyalkylene oxide, the second polyalkylene oxide may correspond to the following formula (II):

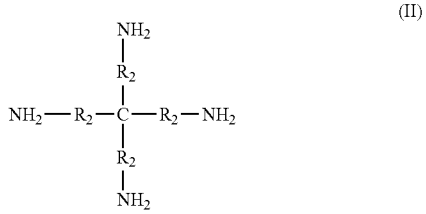

(II)

where $R_2$ can be the same as $R_1$ as described above.

The amine groups in the compounds of formula (II) can be terminally located on the polyalkylene oxide arms or, alternatively, at one or more location along the polyalkylene oxide arms. Likewise, although a single amine group per polyalkylene oxide arm is typical, it is also contemplated that more than one and up to ten or more amine groups per polyalkylene oxide arm may be present.

Where utilized, the polyalkylene oxide backbone of the amine-functional polymer may be a PEG, in embodiments di-, tri- and tetra-functional PEG materials, and/or combinations thereof. In one embodiment, the amine end groups of the amine-functional polymer are primary amine groups, secondary amine groups, or mixtures thereof. Also useful are amino functional dendrimers PAMAM etc., polypeptides, and block or random copolymers of lysine, ornithine or allylamine with other monomers having no amine substitution. Polyoxyalkyleneamines, including those sold under the name JEFFAMINE® by Huntsman Performance Chemicals (Houston, Tex.), may also be used as the amine end groups.

Methods for producing the amine-functional polymer are within the purview of those skilled in the art. Where utilized, an amine-functional polyalkylene oxide can be derived from any $C_2$-$C_6$ alkylene oxide and can be homopolymeric or copolymeric. Thus, for example, the amine-functional polyalkylene oxide can be derived from ethylene oxide and be an amine-functional polyethylene oxide (PEO). As another example, the polyalkylene oxide can be derived from propylene oxide and be an amine-functional polypropylene oxide (PPO). As yet another example, a combination of ethylene oxide and propylene oxide can be used to form a random or block copolymer as the amine-functional polyalkylene oxide. In some embodiments, it can be a commercially available PEG or a PLURONICS® poloxamer.

Altering the number of amine groups present on the amine-functional polymer may be utilized to provide desired physical characteristics to the synthetic absorbable macromer composition of the present disclosure. A greater degree of substitution will provide greater cross-linking which will provide a material that exhibits less swelling and less compliance. A lower degree of substitution will yield a less cross-linked material having greater compliance.

The preparation of amine-functional polyalkylene oxides is within the purview of those skilled in the art. In fact, suitable amine-functional polyalkylene oxides are commercially available from Shearwater Polymers, Inc., Huntsville, Ala. In some embodiments, the amine-functional polyalkylene oxide can be a diamine.

In another embodiment, the amine-functional polyalkylene oxide can have a stiffening linkage within the polymer. In such a case, the polymer backbone can have the formula:

$$H_2N\text{—}[R_3\text{-}Q\text{-}R_4]\text{—}NH_2 \quad (III)$$

where $R_3$ and $R_4$ are the same or different and can be alkoxy, alkoxy with hydrolyzable linkages such as esters, aliphatic esters, carbonates, orthoesters etc., and Q can be a stiffening linkage including groups such as phthalic, bisphenol A, biphenyl, diglycidyl ether of bisphenol A, ethoxylated bisphenol A, terephthalic acid, phenylene diamine, imides, and the like.

The stiffening linkages in formula (III) above can be any group that inhibit flexing of the optionally substituted polymer backbone. Stiffening can be provided by either physical characteristics (steric hindrance) or chemical characteristics (charge repulsion) to inhibit flexing of the stiffening group.

Methods for incorporating these stiffening linkages into a PAO are known to those skilled in the art. In one embodiment, the stiffening linkages may be incorporated by a ring-opening polymerization reaction as follows:

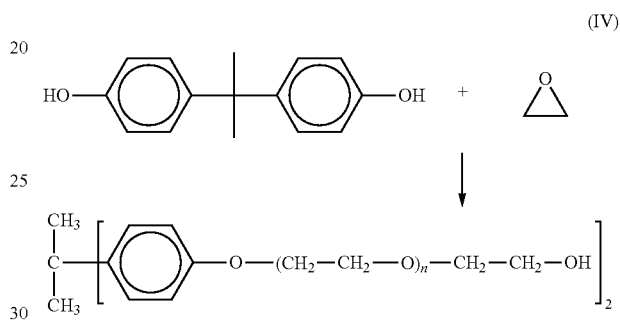

(IV)

In another embodiment, the stiffening linkages may be incorporated by reacting terephthaloyl chloride with excess diamine functionalized PEG in the presence of pyridine following the general reaction scheme below:

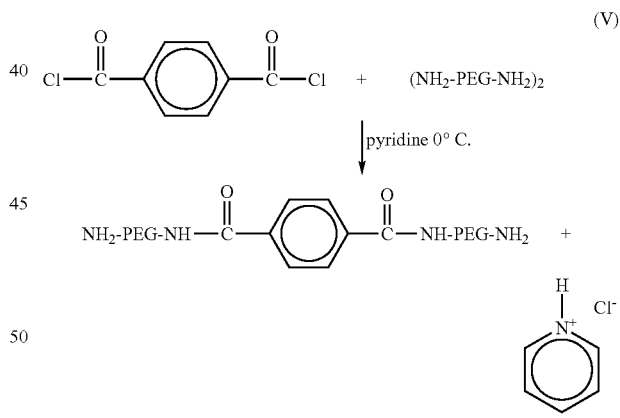

(V)

The amine-functional polymer, like the acid-functional polymer, should have a molecular weight sufficiently high that when crosslinked, the synthetic absorbable macromer composition of the present disclosure provides adequate adhesive properties, but sufficiently low that upon degradation the resulting polymer fragments can be excreted by the body. The molecular weight of the amine-functional polyalkylene oxide may be adjusted to enhance the desired physical characteristics of the final composition. The backbones of the amine-functional polymer can have molecular weights in the range of from about 500 to about 20,000, in embodiments from about 1000 to about 10,000, typically from about 2000 to about 5000.

The amine-functional polymer may be present in the adhesive composition of the present disclosure in amounts ranging from about 80% to about 20% by weight of the adhesive composition, in embodiments from about 67% to about 25% by weight of the adhesive composition, typically from about 50% to about 34% by weight of the adhesive composition.

In some embodiments, where utilized, the polyalkylene oxide backbone of the acid-functional and/or amine-functional polymer can have a branched or multi-arm structure. For example, the polyalkylene oxide backbone can be the result of polymerizing alkylene oxide monomer in the presence of a multi-functional initiator such as a polyhydric initiator. Reaction conditions for producing branched or multi-arm polyalkylene oxide backbones are within the purview of those skilled in the art.

In addition, the acid-functional polymer, the amine-functional polymer, or both, can contain random, infrequently occurring, uncharged and/or non-polar amino acids. Amino acids possessing uncharged polar side chains which may be added to either the first or second polymer include asparagine, glutamine, serine, threonine and tyrosine. Amino acids possessing non-polar side chains which may be added to either the acid-functional or amine-functional polymers include glycine, alanine, valine, leucine, isoleucine, proline, phenylalanine, methionine, tryptophan, and cysteine. In embodiments, combinations of these uncharged and non-polar amino acids may be added to the acid functional polymer, the amine-functional polymer, or both.

The addition of these non-functionalized amino acids can be utilized to adjust the crosslink ratio of the acid-functional polymer with the amine-functional polymer. However, the majority of the acid-functional polymer should be a polymer with at least one pendant acidic group and the majority of the amine-functional polymer should be a polymer with reactive amine groups to maintain the reactive nature of the two polymers for each other and their ability to readily crosslink with each other.

Where present, these non-functionalized amino acids can be present in the synthetic absorbable macromer composition of the present disclosure in amounts from about 1% to about 40% by weight of the synthetic absorbable macromer composition, in embodiments from about 5% to about 35% by weight of the synthetic absorbable macromer composition, typically from about 10% to about 30% by weight of the synthetic absorbable macromer composition.

The exact molecular weight of the synthetic absorbable macromer composition of the present disclosure will depend on a variety of factors, including the degree of substitution of the acid-functional polymer and amine-functional polymer, and the intended use of the resulting composition, for example as an adhesive or sealant. One consideration in selecting the polymer is that the degradation products should be sufficiently small to pass through tissue membranes for disposal by the body. In addition, where the synthetic absorbable macromer composition of the present disclosure is to be used as a sealant, the synthetic absorbable macromer composition should be compliant, yet strong. A balance of these properties is achieved through selection of the polymers.

The degree of substitution of the polymer will be a factor in the amount of crosslinking ultimately achieved and thus in the flexibility of the synthetic absorbable macromer composition. The crosslinking between the acid-functional polymer and the amine-functional polymer can occur via hydrogen bonds and/or hydrophobic bonds. This degree of substitution can be quantified using titrations, or spectrophotometrically with a modified Toluidine Blue assay. (Johnston, "A Simple, Nondestructive Assay for Bound Hyaluronan," J. Biomed. Materials Res. (Applied Biomaterials) 53: 188-191 (2000).) PEGs are commercially available from a variety of sources, including Nektar Therapeutics, 150 Industrial Road, San Carlos, Calif., 94070.

The selection of the polymers can also be adjusted to tailor the synthetic absorbable macromer composition for optimal viscosity according the desired sealant use. Higher viscosities minimize displacement of the sealant. Higher viscosities also improve the retention of uncured or unpolymerized sealants at the site of application. These higher viscosities will, however, make the synthetic absorbable macromer compositions more difficult to apply. A useful range of viscosity for a sealant is from about 200 centipoise ("cP") to about 40,000 cP, in embodiments from about 500 to about 5,000 cP.

In addition to or in place of components that provide hydrolytically degradable linkages, at least one linkage that is enzymatically degradable may be incorporated into the acid-functional polymer, the amine-functional polymer, or both. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetyineuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the polymer.

Coupling agents that are useful in the compositions of the present disclosure which are amine specific reactive reagents include carbodiimides; isothiocyanates; isocyanates; acyl azides; N-hyroxysuccinimide (NHS) esters; and sulfo-NHS esters. Dithiobis-(succinimidyl propionate) (DSP), also known as Lomant's reagent, can be used in aqueous media at a pH between 7 and 9, or it can be prepared with DMSO or DMF to make it water soluble. Dithiobis-(sulfosuccinimidyl propionate) (DTSSP); bis(sulfosuccinimidyl)suberate (BS); disulfosuccinimidyl tartarate; bis[2-(sulfosuccinimidyloxycarbonyloxy)ethyl]sulfone (sulfo-BSOCOES); ethylene glycol bis(sulfosuccinimidylsuccinate) (sulfo-EGS) are other examples of commonly used water soluble sulfo-NHS esters which can be used as coupling agents. N,N'-dissuccinimidyl carbonate (DSC) can also be used in either aqueous or organic media. Additionally, sulfonyl chlorides, anhydrides, carbonates, aldehydes, and glyoxals are all possible coupling agents. Epoxides and oxiranes may also be used.

Other coupling agents which may be utilized include imidoesters, which undergo continuous degradation due to hydrolysis in aqueous media. Such coupling agents are especially suited where short term adhesive use is contemplated. Common imidoesters include dimethyl adipimidate (DMA), dimethyl pimelimidate (DMP), dimethyl suberimidate (DMS), and dimethyl 3,3'-dithiobispropionimidate (DTBP). See, for example, Hermanson, G. T., Bioconjugate Techniques. Academic Press, San Diego. 785 (1996).

Carboxylate specific reactive reagents which may be used include carbodiimides, diazoalkanes and diaziacetyl compounds, and carbonyl diimidazoles. N,N'-carbonyl diimidazole (CDI) is water soluble, but hydrolyzes rapidly in aqueous media. This compound may also be used to activate hydroxyls to react with amines to result in carbamate linkages. See, for example, Hermanson, G. T., Bioconjugate Techniques. Academic Press, San Diego. (1996).

In embodiments, coupling agents utilized in compositions of the present disclosure include carbodiimides. Examples of carbodiimides which can be used as crosslinking agents are 1-ethyl-3-(3-dimethylaminopropyl) carbodiimide hydrochloride (EDC), and 1-cyclohexyl-3-(2-morpholinoethyl) carbodiimide metho-p-toluenesulfonate (CMC). EDC is particularly useful in some embodiments. Suitable coupling agents are commercially available from a variety of sources. For example, EDC is commercially available from Sigma-Aldrich (St. Louis, Mo.); Poly Sciences, Inc. (Warrington, Pa.); and BioVectra dcl (Oxford, Conn.).

To prepare the synthetic absorbable macromer compositions of the present disclosure, the acid-functional polymer is prepared. In some embodiments, the acid-functional polymer may be placed in solution. This first solution can be prepared by simply adding the acid-functional polymer to water and heating with stirring. The temperature to which the solution is heated should be sufficient to cause the acid-functional polymer to go into solution, but insufficient to cause degradation of the acid-functional polymer. Typically, the solution will be heated to a temperature in the range of 0° to 100° C. The solvent employed to make the first aqueous solution is a pharmaceutically acceptable solvent and can, in some embodiments, be water. Additional solvents which may be used as the pharmaceutically acceptable solvent or included as a co-solvent in the first solution include diols, polyols, mineral oil, and isotonic solutions such as Ringer's solution. The amount of the acid-functional polymer added to the solvent depends on the particular substitutions and solvent employed but generally will be in the range of 50 to 500 grams per liter. The amount of acid-functional polymer added should be insufficient to cause precipitation of the polymer upon cooling of the solution to room temperature.

The amine-functional polymer is then prepared. In some embodiments the amine-functional polymer may also be placed in solution. This amine-functional polymer can be prepared in the same manner as the acid-functional polymer solution, with comparable temperature and time; i.e., the temperature to which the solution is heated should be sufficient to cause the amine-functional polymer to go into solution, but insufficient to cause degradation of the amine-functional polymer. Typically, the solution will be heated to a temperature in the range of 0° to 100° C. The solvent employed to make the second amine-functional aqueous solution can be simply water, but may include additional solvents listed above in connection with the first aqueous solution. The amount of the amine-functional polymer added to the solvent depends on the particular substitutions and solvent employed but generally will be in the range of 50 to 500 grams per liter. The amount of amine-functional polymer added should be insufficient to cause precipitation of the amine-functional polymer upon cooling of the solution to room temperature.

The coupling agent may then be added to the acid-functional polymer, the amine-functional polymer, or both. The coupling agent may, in some embodiments, be added to the acid-functional polymer in excess. The amount of coupling agent added will depend on a number of factors including the degree of substitution of acid and/or amine groups and the particular coupling agent employed. Generally, the amount of coupling agent in the compositions of the present disclosure can range from about 0.1% to about 10% by weight of the total composition, in embodiments from about 1% to about 5% by weight of the total composition.

A variety of optional ingredients may be added to the acid-functional polymer, the amine-functional polymer, or both. A phospholipid surfactant that provides antibacterial stabilizing properties and helps disperse other materials in the synthetic absorbable macromer composition may be added. Optional additives include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and anti-anxiety agents, vitamin D preparations, hypoglycemic agents, antiulcer agents, hypnotics, antibiotics, antifungal agents, sedative agents, bronchodilator agents, antiviral agents and dysuric agents.

Additionally, an enzyme may be added to the acid-functional polymer, the amine-functional polymer, or both, to increase the rate of degradation of the synthetic absorbable macromer composition. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease, and the like. In some embodiments, where an enzyme is added, the enzyme may be included in a liposome or microsphere to control the rate of its release, thereby controlling the rate of degradation of the adhesive composition of the present disclosure. Methods for incorporating enzymes into liposomes and/or microspheres are known to those skilled in the art.

The synthetic absorbable macromer compositions of the present disclosure can be used in human and animal medical applications including, but not limited to, wound closure (including surgical incisions and other wounds), adhesives for medical devices (including implants), sealants and void fillers, and embolic agents.

In some embodiments, the acid-functional and amine-functional polymers are kept separate prior to application to tissue. Thus, the first and second aqueous solutions containing the polymers can be dispensed from a conventional two-part adhesive dispenser which provides mixing of the two solutions either prior to or after leaving the dispenser. Such dispensers are disclosed, for example, in U.S. Pat. Nos. 4,978, 336, 4,361,055, 4,979,942, 4,359,049, 4,874,368, and 5,368, 563, the disclosures of which are incorporated herein by reference.

In some embodiments, the acid-functional polymer may be combined with an optional coupling agent, and the acid-functional polymer and coupling agent may then be combined with the amine-functional polymer prior to delivery. In embodiments, the acid-functional polymer and optional coupling agent may be dry and the amine-functional polymer may be in solution.

In other embodiments, especially where the synthetic absorbable macromer composition of the present disclosure is to be utilized as a void filler or sealant to fill a defect in an animal's body, it may be advantageous to more precisely control the conditions and extent of cross-linking; in such a case, it may be desirable to partially cross-link the synthetic absorbable macromer composition prior to its use to fill a void in animal tissue. In such a case the synthetic absorbable macromer composition is applied to the void and allowed to set, thereby filling the void or defect in animal tissue.

The adhesive composition of the present disclosure can be used for a number of different applications. These applications include using the adhesive to bind tissue together either as a replacement of, or as a supplement to, sutures, staples, tapes and/or bandages. Use of the disclosed adhesive can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

Additional applications include sealing tissues to prevent or control blood, or other fluid leaks, at suture or staple lines. In another embodiment, the adhesive composition can be used to attach skin grafts and position tissue flaps during reconstructive surgery. In still another embodiment, the adhesive can be used to close tissue flaps in periodontal surgery.

To effectuate the joining of two tissue edges, the two edges are approximated, and the acid-functional polymer is combined with the amine-functional polymer. Without wishing to be bound to any theory, it is believed that, upon mixing with the coupling agent, the acid/amine groups of the two polymers crosslink with each other thereby forming a hydrogel. The crosslinking reaction is rapid, generally taking less than one minute. It is also believed that the acid/amine groups of the two polymers adhere to tissue by linking directly to acid/amine groups present on the tissue surface. In this case the synthetic absorbable macromer composition of the present disclosure can be used as an adhesive to close a wound, including a surgical incision. Generally, the synthetic absorbable macromer composition is applied to the wound and allowed to set, thereby closing the wound.

In another embodiment, the present disclosure is directed to a method for using the synthetic absorbable macromer composition of the present disclosure to adhere a medical device to tissue, rather than secure two edges of tissue. In some embodiments, depending on the composition of the medical device, a coating having reactive groups to which the coupling agent can bind may be required on the medical device. In some cases such a coating can include the acid-functional polymer or the amine-functional polymer. In some aspects, the medical device includes an implant. Other medical devices include, but are not limited to, pacemakers, stents, shunts and the like. Generally, for adhering a device to the surface of animal tissue, the synthetic absorbable macromer composition of the present disclosure can be applied to the device, the tissue surface or both. The device, adhesive composition and tissue surface are then brought into contact with each other and the synthetic absorbable macromer composition is allowed to set, thereby adhering the device and surface to each other.

The present adhesive can also be used to prevent post surgical adhesions. In such an application, the adhesive composition is applied and cured as a layer on surfaces of internal tissues in order to prevent the formation of adhesions at a surgical site during the healing process.

When used as a sealant, the synthetic absorbable macromer composition of the present disclosure can be used in surgery to prevent or inhibit bleeding or fluid leakage both during and after a surgical procedure. It can also be applied to prevent air leaks associated with pulmonary surgery. The sealant is applied directly to the desired area in at least an amount necessary to seal off any defect in the tissue and seal off any fluid or air movement.

Application of the adhesive or sealant, with or without other additives, can be done by any conventional means. These include dripping, brushing, or other direct manipulation of the adhesive on the tissue surface, or spraying of the adhesive to the surface. In open surgery, application by hand, forceps or the like is contemplated. In endoscopic surgery, the adhesive can be delivered through the cannula of a trocar, and spread at the site by any device known in the art.

It will be understood that various modifications may be made to the embodiments disclosed herein. Therefore the above description should not be construed as limiting, but merely as exemplifications of typical embodiments. Those skilled in the art will envision other modifications within the scope and spirit of the claims appended hereto.

What is claimed is:

1. A synthetic absorbable macromer composition comprising:

an acid-functional polymer of formula (I):

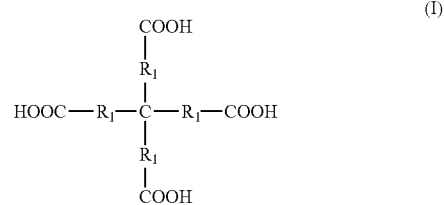

where $R_1$ can be the same or different at each location and is selected from the group consisting of polyalkylene oxides, polyethylene glycols having degradable linkages, and polyethylene oxide-polypropylene oxide copolymers;

an amine-functional polymer comprising a polyalkylene oxide having at least one pendant amine group and a non-pendant, non-terminal, intra-backbone stiffening linkage, the stiffening linkage selected from the group consisting of phthalic groups, bisphenol A, biphenyl groups, diglycidyl ethers of bisphenol A, ethoxylated bisphenol A, terephthalic acid, phenylene diamine, and imides; and a coupling agent comprising a carbodiimide.

2. A synthetic absorbable macromer composition as in claim 1, wherein $R_1$ comprises a polyethylene glycol.

3. A synthetic absorbable macromer composition as in claim 2, wherein the polyethylene glycol is selected from the group consisting of di-functional materials, tri-functional materials, tetra-functional materials and combinations thereof.

4. A synthetic absorbable macromer composition as in claim 1, wherein the acid-functional polymer further comprises at least one hydrolytically degradable component.

5. A synthetic absorbable macromer composition as in claim 1, wherein the acid-functional polymer further comprises at least one enzymatically degradable linkage.

6. A synthetic absorbable macromer composition as in claim 1, wherein the acid-functional polymer further comprises a non-functionalized amino acid selected from the group consisting of asparagine, glutamine, serine, threonine, tyrosine, glycine, alanine, valine, leucine, isoleucine, proline, phenylalanine, methionine, tryptophan, cysteine, and combinations thereof.

7. A synthetic absorbable macromer composition as in claim 1, wherein the acid-functional polymer is present in a range from about 20% to about 80% by weight of the synthetic absorbable macromer composition.

8. A synthetic absorbable macromer composition as in claim 1, wherein the amine-functional polymer is a polyamino acid selected from the group consisting of polylysine, polyornithine, polycysteine, polyarginine, polyhistidine, and combinations thereof.

9. A synthetic absorbable macromer composition as in claim 1, wherein the amine-functional polymer comprises a compound of formula (II):

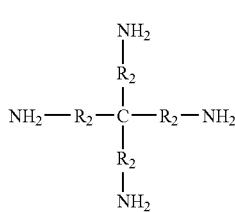

where $R_2$ can be the same or different at each location and is selected from the group consisting of polyalkylene oxides, polyethylene glycols having degradable linkages, and polyethylene oxide-polypropylene oxide copolymers, wherein at least one $R_2$ possesses a stiffening linkage selected from the group consisting of phthalic groups, bisphenol A, biphenyl groups, diglycidyl ethers of bisphenol A, ethoxylated bisphenol A, terephthalic acid, phenylene diamine, and imides.

10. A synthetic absorbable macromer composition of claim 9 wherein $R_2$ is a polyethylene glycol.

11. A synthetic absorbable macromer composition as in claim 10, wherein the polyethylene glycol is selected from the group consisting of di-functional materials, tri-functional materials, tetra-functional materials and combinations thereof.

12. A synthetic absorbable macromer composition as in claim 10, wherein the polyethylene glycol is terminated with amine end groups selected from a group consisting of primary amines, secondary amines, and combinations thereof.

13. A synthetic absorbable macromer composition as in claim 9, wherein the amine-functional polymer further comprises a non-functionalized amino acid selected from the group consisting of asparagine, glutamine, serine, threonine, tyrosine, glycine, alanine, valine, leucine, isoleucine, proline, phenylalanine, methionine, tryptophan, cysteine, and combinations thereof.

14. A synthetic absorbable macromer composition as in claim 9, wherein the amine-functional polymer further comprises at least one hydrolytically degradable component.

15. A synthetic absorbable macromer composition as in claim 9, wherein the amine-functional polymer further comprises at least one enzymatically degradable linkage.

16. An synthetic absorbable macromer composition as in claim 1, wherein the amine-functional polymer is present in a range from about 80% to about 20% by weight of the total synthetic absorbable macromer composition.

17. A synthetic absorbable macromer composition as in claim 1, wherein the carbodiimide is 1-ethyl -3(3-dimethylamino propyl)-carbodiimide hydrochloride.

18. An adhesive for wound closure comprising the synthetic absorbable macromer composition of claim 1.

19. A sealant for use in a medical application comprising the synthetic absorbable macromer composition of claim 1.

20. A method for closing a wound comprising:
applying the synthetic absorbable macromer composition of claim 1 to said wound; and
allowing the synthetic absorbable macromer composition to set thereby closing said wound.

21. The method of claim 20 wherein the wound is a surgical incision.

22. A method for filling a void in animal tissue comprising:
applying the synthetic absorbable macromer composition of claim 1 to said void; and
allowing the synthetic absorbable macromer composition to set thereby filling said void.

23. A method for adhering a medical device to a surface of animal tissue comprising the steps of:
applying the synthetic absorbable macromer composition of claim 1 to said device, said surface or both;
bringing the device, synthetic absorbable macromer composition and surface into contact with each other; and
allowing the synthetic absorbable macromer composition to set thereby adhering the device and surface to each other.

24. The method of claim 23 wherein said medical device is an implant.

\* \* \* \* \*